United States Patent [19]
Arhancet

[11] Patent Number: 5,446,220
[45] Date of Patent: Aug. 29, 1995

[54] METHODS FOR INHIBITING VINYL AROMATIC MONOMER POLYMERIZATION

[75] Inventor: Graciela B. Arhancet, Katy, Tex.

[73] Assignee: Betz Laboratories, Inc., Trevose, Pa.

[21] Appl. No.: 295,311

[22] Filed: Aug. 24, 1994

[51] Int. Cl.$^6$ .............................................. C07C 7/20
[52] U.S. Cl. ........................................ 585/5; 585/3; 585/4
[58] Field of Search ................................ 585/5, 4, 3

[56] References Cited

U.S. PATENT DOCUMENTS

| | | | |
|---|---|---|---|
| 4,105,506 | 12/1977 | Watson et al. | 203/9 |
| 4,466,905 | 8/1987 | Butler et al. | 252/403 |
| 4,720,566 | 1/1988 | Martin | 558/306 |
| 4,774,374 | 9/1988 | Abruscato et al. | 585/24 |
| 5,245,760 | 10/1993 | Winter et al. | 585/5 |

FOREIGN PATENT DOCUMENTS

| | | | |
|---|---|---|---|
| 163428 | 6/1976 | Czechoslovakia . | |
| 0240297 | 10/1987 | European Pat. Off. . | |
| 594341 | 4/1994 | European Pat. Off. | 585/5 |

*Primary Examiner*—Asok Pal
*Attorney, Agent, or Firm*—Alexander D. Ricci; Philip H. Von Neida

[57] ABSTRACT

Methods for inhibiting the polymerization of vinyl aromatic monomers in oxygen-free processing systems are disclosed. These methods comprise adding from 1 to about 10,000 parts per million parts monomer of a combination of a dinitrophenol compound, a hydroxylamine compound and a phenylenediamine compound. Preferably, 2-sec-butyl-4,6-dinitrophenol or 4,6-dinitro-o-cresol are used in combination with bis-(hydroxypropyl)hydroxylamine and N,N'-di-sec-butyl-p-phenylenediamine.

10 Claims, No Drawings

METHODS FOR INHIBITING VINYL AROMATIC MONOMER POLYMERIZATION

FIELD OF THE INVENTION

This invention relates to methods for inhibiting the unwanted polymerization of vinyl aromatic monomers during their processing in an oxygen-free environment.

BACKGROUND OF THE INVENTION

Common industrial methods for producing styrene typically include separation and purification processes such as distillation to remove unwanted impurities. Unfortunately, purification processes carried out at elevated temperatures result in an increased rate of undesired polymerization. Distillation is generally carried out under vacuum to minimize loss of monomer. The presence of oxygen, although virtually excluded in styrene distillation, will also promote polymerization of the monomer.

This polymerization results not only in loss of desired monomer end-product, but also in the loss of production efficiency caused by polymer formation and/or agglomeration of polymer on process equipment. Thermal polymerization of styrene monomer results in the formation of normal (i.e., linear) polymer. This resulting polystyrene polymer is characterized by its glassy and transparent appearance and its solubility in the styrene monomer and many organic solvents.

SUMMARY OF THE INVENTION

Disclosed are methods for inhibiting the polymerization of vinyl aromatic monomers during their processing in an oxygen free environments. The present inventor has discovered that a combination of a dinitrophenol compound, a hydroxylamine compound and a phenylenediamine compound provide enhanced polymerization inhibition in oxygen-free vinyl aromatic monomers.

DESCRIPTION OF THE RELATED ART

The compounds generally used commercially to prevent polymerization of vinyl aromatic monomers are of the dinitrophenolic type. For example, U.S. Pat. No. 4,105,506, Watson et al., teaches the use of 2,6-dinitro-p-cresol as polymerization inhibitor of vinyl aromatic compounds. U.S. Pat. No. 4,466,905, Butler et al., teaches that 2,6-dinitro-p-cresol and p-phenylenediamines will inhibit polymerization in the distillation column if a minimum amount of oxygen is present. When this amount of oxygen is decreased, polymerization in the column is substantially increased. U.S. Pat. No. 4,774,374, Abruscato et al., teaches compositions and processes for inhibiting the polymerization of a vinyl aromatic compound employing an oxygenated species formed by the reaction of oxygen and a N-aryl-N'-alkyl-p-phenylenediamine. U.S. Pat. No. 4,720,566, Martin, teaches methods and compositions for inhibiting polymerization of acrylonitrile in the quench tower, no oxygen excluded, using a hydroxylamine compound and a phenyl p-phenylenediamine compound.

Czechoslovakia Patent No. 163,428 teaches a method for stabilizing styrene and divinylbenzene utilizing 2,4-dinitroorthocresol and diethylhydroxylamine. European Patent Application 0 240 297 also teaches the use of this combination to inhibit polymerization of styrene. Both these disclosures treat systems at lower temperatures and higher oxygen contents. The use of diethylhydroxylamine however is problematic in styrene purification processes as it has a boiling point (125° to 130° C. at 760 mm Hg) similar to styrene and will carry over with the styrene during purification processing.

A variety of inhibitor compositions have been employed in styrene and other vinyl aromatic monomers to inhibit undesirable polymerization. Amongst others, agents that have been used include sulfur, p-benzoquinone, phenylenediamines, tert-butyl pyrocatechol, phenothiazine, hydroxylamines, nitrocompounds, and hindered phenols. However, many of these compounds present disadvantages such as high toxicity, instability and explosion hazard under elevated temperature, or insufficient efficacy under processing conditions (i.e., inhibitor requires oxygen to be effective). The present inventor has discovered a novel method for inhibiting vinyl aromatic monomer polymerization that avoids these problems associated with known inhibitors.

DETAILED DESCRIPTION OF THE INVENTION

The present invention provides for methods for inhibiting the polymerization of vinyl aromatic monomers in an oxygen-free processing system comprising adding to the monomers a polymerization inhibiting amount of a dinitrophenol compound, a hydroxylamine compound and a phenylenediamine compound.

The methods of the present invention prove efficacious at inhibiting the polymerization of vinyl aromatic monomers, particularly styrene, during their processing under oxygen-free monomer processing conditions. These processing conditions include but are not limited to purification and distillation of vinyl aromatic monomers.

The phrase "oxygen-free processing conditions" is meant to define the substantially oxygen-free conditions under which vinyl aromatic monomer, particularly styrene are processed. These conditions, exemplified by but not limited to distillation and purification processes, generally have less than 2 parts per million parts oxygen present and preferably less than one part per million parts oxygen present. Pure styrene saturated with air at room temperature contains about 60 parts per million of dissolved oxygen.

The dinitrophenol compounds generally have the structure

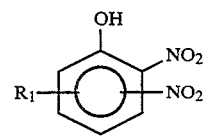

wherein $R_1$ is hydrogen or $C_1$ to $C_{12}$ alkyl.

Preferred dinitrophenol compounds include but are not limited to 4,6-dinitro-o-cresol (DNOC), 2,6-dinitro-p-cresol (DNPC) and 2-sec-butyl-4,6-dinitrophenol (DNBP).

The hydroxylamine compounds useful in this invention generally have the formula

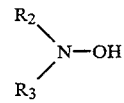

wherein $R_2$ and $R_3$ are the same or different and are hydrogen, alkyl, aryl, alkaryl, aralkyl, or hydroxyalkyl groups and preferably have about three to about twenty carbon atoms, except when $R_2$ is H, then $R_3$ is $C_6$ alkyl to $C_{20}$ alkyl. The preferred hydroxylamine compound is bis-hydroxypropylhydroxylamine (HPHA).

The phenylenediamine compounds useful in this invention generally have the formula:

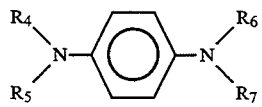

wherein $R_4$, $R_5$, $R_6$ and $R_7$ are the same or different and are hydrogen, alkyl, aryl, alkaryl or aralkyl groups having from one to about twenty carbon atoms. The preferred phenylenediamine compound is N,N'-di-sec-butyl-p-phenylenediamine.

The methods of the present invention prove effective at inhibiting the polymerization of vinyl aromatic monomers during oxygen-free processing. The inventive methods provide enhanced activity or synergistic activity over each separate component at inhibiting polymerization of vinyl aromatic monomer undergoing distillation and purification processes at elevated temperatures. Styrene, for example, is typically processed at temperatures between 95° and 125° C. The methods of the present invention provide particular efficacy in higher temperature (i.e., >110° C.) styrene monomer processing systems.

The total amount of dinitrophenol compound, hydroxylamine compound and phenylenediamine compound used in the methods of the present invention is that amount which is sufficient to inhibit polymerization and will vary according to the conditions under which the vinyl aromatic monomer is being processed and exposed to high temperatures. At higher temperatures and higher monomer contamination, larger amounts of the polymerization inhibiting composition are required.

Preferably, the total amount of polymerization inhibiting combination added to the vinyl aromatic monomer ranges from 1 to about 10,000 parts per million parts of monomer. More preferably, the range is from about 5 parts to about 500 parts of the combination per million parts of monomer.

The weight ratio of dinitrophenol compound to hydroxylamine compound to phenylenediamine compound ranges from 1:9:1 to 9:1:9 with a weight ratio of 1:1:1 preferred.

The combinations of the present invention can be added to the vinyl aromatic monomer by any conventional method, either as individual ingredients or as a combination of ingredients. It is preferred that the individual ingredients are added to the monomer as a single treatment.

The combination of the present invention may be added to the vinyl aromatic monomer as either a dispersion or as a solution using a suitable liquid carrier or solvent. Any solvent that is compatible with the individual ingredients of the composition and the vinyl aromatic monomer may be employed.

Accordingly, it is possible therefor to produce a more effective vinyl aromatic monomer polymerization inhibition treatment than is obtainable by the use of any one ingredient alone when measured at comparable treatment levels. This enhanced activity, particularly at temperatures of 110° C. or greater, allows for the concentration of each of these ingredients to be lowered and the total quantity of polymerization inhibitor required, particularly at higher processing temperatures, may be reduced.

The preferred inventive embodiments employ bis-(hydroxypropyl) hydroxylamine and N,N'-di-sec-butyl-p-phenylenediamine with 4,6-dini-tro-o-cresol and 2-sec-butyl-4,6-dinitrophenol, respectively.

This invention will now be further described with reference to a number of specific examples which are to be regarded solely as illustrative and not as restricting the scope of the invention.

EXAMPLES

In order to evaluate the improved polymerization inhibition of the inventive combinations and to demonstrate the enhanced activity of the combination, styrene polymerization testing was performed.

Uninhibited styrene (5 mL) was placed in a test tube and the appropriate amount of treatment was added. The tube was capped with a septum and argon was bubbled through the liquid at 15 mL/min for 3 minutes. Then, the tubes were placed in an oil bath heated to 120° C. for 2 hours. The amount of polystrene formed was determined by methanol precipitation. Results of this testing are reported in Table I.

TABLE I

Styrene Polymerization Test
Uninhibited Styrene
120° C.

| Treatment | Dose (ppm) | Percent Polymer |
|---|---|---|
| Blank | — | 23.3 |
| DNOC | 300 | 2.15 |
| DNBP | 300 | 1.77 |
| PDA | 300 | 21.06 |
| HPHA | 300 | 17.96 |
| PDA:HPHA:DNOC | 100:100:100 | 1.38 |
| PDA:HPHA:DNOC | 75:150:75 | 1.78 |
| PDA:HPHA:DNOC | 50:150:100 | 1.23 |
| PDA:HPHA:DNBP | 100:100:100 | 1.02 |
| PDA:HPHA:DNBP | 50:150:100 | 0.79 |

DNOC is 4,6-dinitro-o-cresol
DNBP is 2-sec-butyl-4,6-dinitrophenol
PDA is N,N'-di-sec-butyl-p-phenylenediamine
HPHA is bis-(hydroxypropyl)hydroxylamine These test results demonstrate the enhanced polymerization inhibition of the three component combination. Unexpected results were evidenced in a range from 1:1:1 to 1:3:2 at inhibiting styrene polymerization at higher (120° C.) styrene processing temperatures.

Uninhibited styrene (100 mL) was placed in a 250 mL three-necked flask fitted with a bubbler, a septa and a condenser. The appropriate treatment was added and argon was bubbled through the solution at 10 mL/min for 10 minutes. Then, the flask was immersed in an oil bath heated to 120° C. and samples were taken every 30 minutes. The amount of polymer formed was determined by methanol precipitation. Results of this testing are shown in Table II.

TABLE II

Styrene Polymerization Test
Uninhibited styrene
120° C.
Treatment: PDA/HPHA/DNBP in a 200:200:100 ppm ratio

| Time (hrs.) | % Polymer |
|---|---|
| 1 | 0.07 |
| 2 | 0.31 |
| 3 | 0.49 |

TABLE II-continued

Styrene Polymerization Test
Uninhibited styrene
120° C.
Treatment: PDA/HPHA/DNBP in a 200:200:100 ppm ratio

| Time (hrs.) | % Polymer |
| --- | --- |
| 4 | 1.10 |

PDA is N,N'-di-sec-butyl-p-phenylenediamine
HPHA is bis-(hydroxypropyl)hydroxylamine
DNBP is 2-sec-butyl-4,6-dinitrophenol The testing results reported in Table II demonstrate that the three component combination provides polymerization inhibition in an oxygen-free environment over an extended time period at elevated temperatures.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what I claim is:

1. A method for inhibiting the polymerization of vinyl aromatic monomers in an oxygen-free vinyl aromatic monomer processing system comprising adding an effective polymerization inhibiting amount of a dinitrophenol compound, a hydroxylamine compound, and a phenylenediamine compound.

2. The method as claimed in claim 1 wherein said dinitrophenol compound has the formula

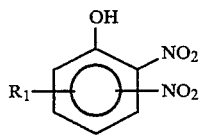

wherein $R_1$ is hydrogen or $C_1$ to $C_{12}$ alkyl.

3. The method as claimed in claim 1 wherein said dinitrophenol compound is selected from the group consisting of 4,6-dinitro-o-cresol, 2,6-dinitro-p-cresol and 2-sec-butyl-4,6-dinitrophenol.

4. The method as claimed in claim 1 wherein said hydroxylamine compound has the formula

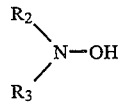

wherein $R_2$ and $R_3$ are the same or different and are hydrogen, alkyl, aryl, alkaryl, aralkyl, or hydroxyalkyl groups and preferably have about three to about twenty carbon atoms, except when $R_2$ is H, then $R_3$ is $C_6$ alkyl to $C_{20}$ alkyl.

5. The method as claimed in claim 1 wherein said hydroxylamine compound is bis-hydroxypropylhydroxylamine.

6. The method as claimed in claim 1 wherein said phenylenediamine compound has the formula:

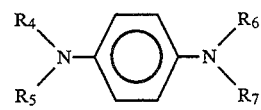

wherein $R_4$, $R_5$, $R_6$ and $R_7$ are the same or different and are hydrogen, alkyl, aryl, alkaryl or aralkyl groups having one to about twenty carbon atoms.

7. The method as claimed in claim 1 wherein said phenylenediamine compound is N,N'-di-sec-butyl-p-phenylenediamine.

8. The method as claimed in claim 1 wherein said dinitrophenol compound, hydroxylamine compound and phenylenediamine compound are added to said vinyl aromatic monomer in an amount ranging from 1 to about 10,000 parts per million parts monomer.

9. The method as claimed in claim 1 where said vinyl aromatic monomer has a temperature of 110° C. or higher.

10. The method as claimed in claim 1 wherein said vinyl aromatic monomer is styrene.

* * * * *